(12) United States Patent
Elst et al.

(10) Patent No.: US 8,076,498 B2
(45) Date of Patent: Dec. 13, 2011

(54) METHOD FOR PREPARING FATTY ACID ESTERS WITH ALCOHOL RECYCLING

(75) Inventors: Kathy Elst, Dessel (BE); Luc Van Ginneken, Balen (BE); Jo Sijben, Etten-Leur (NL)

(73) Assignee: Vlaamse Instelling Voor Technologisch Onderzoek N.V. (Vito), Mol (BE)

( * ) Notice: Subject to any disclaimer, the term of this patent is extended or adjusted under 35 U.S.C. 154(b) by 169 days.

(21) Appl. No.: 12/522,668

(22) PCT Filed: Jan. 10, 2008

(86) PCT No.: PCT/EP2008/050259
§ 371 (c)(1), (2), (4) Date: Jul. 9, 2009

(87) PCT Pub. No.: WO2008/084084
PCT Pub. Date: Jul. 17, 2008

(65) Prior Publication Data
US 2010/0048930 A1 Feb. 25, 2010

(30) Foreign Application Priority Data
Jan. 10, 2007 (EP) .................................... 07100314

(51) Int. Cl.
C07C 51/00 (2006.01)
(52) U.S. Cl. ........................................................ 554/175
(58) Field of Classification Search ............... 554/175
See application file for complete search history.

(56) References Cited

U.S. PATENT DOCUMENTS
2002/0035282 A1 3/2002 Suppes

FOREIGN PATENT DOCUMENTS
| EP | 0 985 654 A1 | 9/1999 |
| EP | 1 298 192 A1 | 12/2001 |
| EP | 1298192 | * 4/2003 |
| WO | WO 95/02661 | 1/1995 |
| WO | WO 2005/021697 A1 | 3/2005 |

OTHER PUBLICATIONS

Fukuda et al., "Biodiesel fuel production by transesterification of oils," *Journal of Bioscience and Bioengineering* (2001) 92 (5): 405-416.
Schwab et al., "Preparation and properties of diesel fuels from vegetable oils," *Fuel* (1987) 66: 1372-1378.
Saka et al., "Biodiesel fuel from rapeseed oil as prepared in supercritical methanol," *Fuel* (2001) 80: 225-231.
Perry et al., *Perry's Chemical Engineer's Handbook* (1997), McGraw-Hill: 13-25-13-26.
PCT Request for International Application PCT/BE2008/050259, 2008.

(Continued)

*Primary Examiner* — Deborah D Carr
(74) *Attorney, Agent, or Firm* — Merchant & Gould P.C.

(57) ABSTRACT

A method produces fatty acid esters by transesterification of fats and oils with the aid of an alcohol, at a high pressure and temperature. Unreacted alcohol is separated inline from the reaction mixture and continuously recycled into the transesterification process. The separation is performed by obtaining a vapour phase and higher density phases of the reaction mixture and concentrating the alcohol in the vapour phase.

16 Claims, 3 Drawing Sheets

OTHER PUBLICATIONS

Form PCT/ISA/237 for International Application PCT/BE2008/050259, 2008.
Form PCT/IPEA/409 for International Application PCT/BE2008/050259, 2008.
Form PCT/IPEA/401 for International Application PCT/BE2008/050259, 2008.
Form PCT/IB/306 for International Application PCT/BE2008/050259, 2008.
Form PCT/ISA/202 for International Application PCT/BE2008/050259, 2008.
Form PCT/IB/304 for International Application PCT/BE2008/050259, 2008.
Form PCT/IB/301 for International Application PCT/BE2008/050259, 2008.
Form PCT/RO/105 for International Application PCT/BE2008/050259, 2008.
Form PCT/ISA/220 for International Application PCT/BE2008/050259, 2008.
Form PCT/IB/308 for International Application PCT/BE2008/050259, 2008.
Form PCT/IB/332 for International Application PCT/BE2008/050259, 2008.
Form PCT/IPEA/416 for International Application PCT/BE2008/050259, 2008.
Acknowledgement of Receipt from EPO for International Application PCT/BE2008/050259, 2008.

* cited by examiner

METHOD FOR PREPARING FATTY ACID ESTERS WITH ALCOHOL RECYCLING

This application is a National Stage Application of PCT/EP2008/050259, filed Jan. 10, 2008, which claims benefit of Serial No. 07100314.9, filed Jan. 10, 2007 in the EPO and which application(s) are incorporated herein by reference. To the extent appropriate, a claim of priority is made to each of the above disclosed applications.

FIELD OF THE INVENTION

The present invention is related to a method and an apparatus for the production of fatty acid esters by transesterification of fats and oils with the aid of an alcohol.

STATE OF THE ART

Because of the world's increasing energy demand and the limited availability of fossil fuels, much research is directed towards development and improvement of alternative renewable fuels. Low-molecular-weight organic liquids can be produced from biomass and can be used or are proposed as fuel for vehicles.

There are several ways of transforming vegetable oils or animal fats—either virgin or waste—into an alternative fuel. The most promising is believed to be transesterification, in which fatty acid esters are produced from the fats and oils, with the aid of an alcohol. As an example, the methyl ester of vegetable oil, known as "bio diesel", is very similar to conventional diesel fuel, and can be used in a conventional diesel engine without any modification.

The base-catalyzed or acid-catalyzed transesterification of the triglycerides in vegetable oil with a simple alcohol such as methanol to form glycerol and the fatty acid methyl esters (FAMEs) has been the preferred method for a long time (Swab et al., 1987). However, a relatively long reaction time is needed when using either an acidic (1-45 hours) or basic (1-8 hours) catalyst to form the esters (Saka and Kusdiana, 2001). In addition, for alkali-catalyzed transesterification, the triglycerides and alcohol must be substantially anhydrous because water causes a partial reaction change to saponification, producing soap. The soap consumes the catalyst, reduces the catalytic efficiency and causes an increase in viscosity, which renders it difficult to achieve a separation of glycerol (Fukuda et al., 2001).

Free fatty acids, which are present in commercially available crude oils and fats, are also known to react with the alkaline catalyst in the conventional transesterification process and form saponified products during the transesterification reactions for bio diesel fuel production. This makes downstream processing (i.e. removal and separation of both the catalyst and the saponified products from the glycerol and the fatty acid methyl esters) quite complex and renders the production of bio diesel quite costly.

To overcome the problems associated with the conventional, acid-catalyzed or base-catalyzed process, supercritical alcohols are used as an alternative reaction medium, without a catalyst. A fluid is supercritical if the substance is above both its critical temperature and critical pressure. A supercritical fluid has a density close to that of its liquid phase, and a viscosity close to that of its gaseous phase. Hence, a fluid in supercritical state functions as a non-liquid solvent and can facilitate a transesterification reaction.

European patent EP 0985654 relates to a method for producing fatty acid esters from oil-and-fat and an alcohol by conducting a reaction under such conditions that at least one of the fats and oils and the alcohol is in a supercritical state in the absence of catalyst. The prepared fatty acid esters are useful as fuels such as diesel fuels, lubrication base oils or fuel additives.

Patent application EP 1298192 discloses a method of preparation of fatty acid esters by transesterification of fats and oils with methanol, in which methanol is fed to the reactor in a supercritical state. The reaction mixture discharged from the reactor is fully depressurized and fed to an alcohol-separation column. In this column, unreacted alcohol is separated and the alcohol-free reaction mixture is collected in a drum. The alcohol-free reaction mixture is further purified and the unreacted and/or intermediate products are recycled into the reactor.

REFERENCES

Fukuda, H., Kondo, A. and Noda, H., J. Biosci. Bioeng., 92 (2001), p. 405.
Saka, S. and Kusdiana, D. Fuel, 80 (2001), p. 225.
Swab, A. W., Bagby, M. O. and Freedman, B. Fuel, 66 (1987), p. 1372.

AIMS OF THE INVENTION

The present invention aims to provide a method and an apparatus for the continuous production of fatty acid esters by transesterification of fats and oils with the aid of an alcohol at high temperature and high pressure, which improve the energy-efficiency of the process compared to the transesterification processes and apparatuses of the prior art.

SUMMARY OF THE INVENTION

In the high-temperature transesterification processes of the prior art, comprising processes in which an alcohol in supercritical state is used, the reaction mixture obtained from the transesterification reaction is depressurized and the unreacted alcohol is extracted from the reaction mixture using distillation, such as vacuum distillation, or extraction resulting in an alcohol-free product stream. As the reaction mixture is at considerable pressure and temperature, a large amount of energy is wasted.

The present invention proposes to use a continuous alcohol recycling system by allowing a minimal depressurization and/or cooling of the reaction mixture. Thereafter, the reaction mixture is fed to a separation system, in order to obtain at least an alcohol-rich stream and an alcohol-poor product stream. The alcohol-rich stream comprises less than 10 wt % of reaction products, intermediates and unreacted oil. The alcohol-rich stream is collected and re-used online in the process. Additional energy improvements may be performed by heat exchange between feed and product stream.

Hence, in the method and apparatus of the present invention, the unreacted alcohol is separated online and continuously recycled into the transesterification process. The separation is performed in a separation system with adjusted process conditions. The separation is based on a change of pressure and a partial cooling of the reaction mixture, such that from the reaction mixture multiple phases form, comprising a vapour phase and one or more phases with higher density than the vapour phase. The one or more phases with higher density may be liquid phases. The unreacted alcohol is concentrated in the vapour phase and the reaction products, intermediates and unreacted oil are concentrated in the one or more phases with higher density (liquid phases).

The invention is related to a method for preparing fatty acid esters by transesterification of fats and/or oils and an alcohol, as set out in the appended claims, wherein the unreacted alcohol is continuously recycled to the transesterification process.

According to an aspect of the invention, there is provided a method of producing fatty acid esters by means of transesterification of fats and/or oils and an alcohol. The method comprises the steps of:

supplying the fats and/or oils and the alcohol to a reactor,
reacting the fats and/or oils with the alcohol at a temperature above 240° C. and a pressure above 0.5 MPa to obtain a reaction mixture comprising unreacted alcohol,
separating the reaction mixture to obtain a first stream comprising a large fraction of the unreacted alcohol and a second stream comprising a small fraction of the unreacted alcohol and
continuously recycling said first stream to the reactor. In the reacting step, the alcohol may or may not be supercritical.

The first stream, which is continuously recycled, comprises at least 90 weight % unreacted alcohol. The fraction unreacted alcohol in the second stream is smaller than in the first stream.

Preferably, the separating step comprises the step of depressurizing the reaction mixture to a pressure equal to or higher than 0.1 MPa. More preferably, the depressurizing step depressurizes the reaction mixture to a pressure in the range between 0.2 MPa and 3 MPa.

Preferably, in the depressurizing step, the reaction mixture is depressurized to a pressure falling in the range between 0.1 MPa and 3 MPa, more preferably between 0.1 MPa and 1.2 MPa.

The separating step is performed at the pressure obtained in the depressurizing step. The depressurizing step is performed prior to the separation of the reaction mixture.

The pressures in the present document refer to absolute pressures.

Preferably, the separating step comprises the step of cooling the reaction mixture to a temperature equal to or higher than 60° C. More preferably, the cooling step cools the reaction mixture to a temperature in the range between 60° C. and 350° C. Even more preferably, the reaction mixture is cooled to a temperature in the range between 120° C. and 300° C.

In the separating step, the step of cooling the reaction mixture refers to a cooling prior to separation of the reaction mixture into two or more streams. The cooling is preferably performed prior to feeding the reaction mixture to a means for separating.

Preferably, a partial (or initial) cooling step is performed prior to the depressurizing step. In the partial cooling step, the reaction mixture can be cooled to a temperature falling in the range between 100° C. and 300° C., preferably between 120° C. and 300° C.

Preferably, in the partial cooling step, the reaction mixture is cooled to a temperature falling in the range between 200° C. and 280° C.

Preferably, the reacting step comprises the use of a catalyst comprising (or consisting of) MgO.

According to the method of the invention, the separating step preferably comprises the steps of:

separating the reaction mixture to obtain a third stream comprising a large fraction of unreacted alcohol and the second stream comprising a small fraction of unreacted alcohol and
separating the third stream to obtain the first stream and a fourth stream, the first stream comprising a fraction of unreacted alcohol which is larger than the fraction of unreacted alcohol of the third stream.

Hence, the first stream may be obtained by a one-stage or a multi-stage separation of the reaction mixture. The multi-stage separation may be preferable for some specific reaction mixture streams.

Preferably, the first stream is a vapour phase. More preferably, the third stream is a vapour phase.

According to a preferred embodiment, the step of continuously recycling the first stream to the reactor comprises the step of condensing the first stream.

Preferably, the cooling step comprises the step of bringing the third stream at a temperature in the range between 60° C. and 350° C. More preferably, the cooling step comprises the step of bringing the first stream at a temperature in the range between 40° C. and 100° C.

In the method of the invention, all the steps are preferably performed continuously. The reaction mixture may comprise water.

According to a second aspect of the invention, there is provided an apparatus for producing fatty acid esters from fats or oils and an alcohol. The apparatus of the invention comprises: a reactor for reacting the fats and/or oils with the alcohol according to a transesterification reaction and obtain a reaction mixture comprising unreacted alcohol; a depressurizer for partially depressurizing the reaction mixture; means for separating the reaction mixture in a first stream comprising a large fraction of unreacted alcohol and a second stream comprising a small fraction of unreacted alcohol and means for continuously recycling said first stream into said reactor.

Preferably, the apparatus further comprises a cooler for partially cooling the reaction mixture. More preferably, the means for continuously recycling comprise a condenser.

The cooler is preferably arranged upstream the depressurizer.

Preferably, the means for separating the reaction mixture is arranged for obtaining a vapour phase, being the first stream, and the second stream. The second stream has a higher average density than the density of the vapour phase and separates from the vapour phase.

Preferably, the means for separating the reaction mixture comprise a distillation column. Equally preferably, the means for separating the reaction mixture comprise a flash separator.

Preferably, the means for separating the reaction mixture is arranged to operate at a temperature in the range between 40° C. and 350° C., more preferably, at a temperature in the range between 60° C. and 350° C. and even more preferably, at a temperature in the range between 120° C. and 300° C.

Preferably, the means for separating the reaction mixture is arranged to operate at a pressure higher than 0.1 MPa, more preferably at a pressure in the range between 0.2 and 3 MPa.

According to a preferred embodiment of the apparatus of the invention, the means for separating the reaction mixture comprise multiple separating means arranged serially for purifying the first stream. The separating means may be flash separators or distillation columns, or a combination of both.

DETAILED DESCRIPTION OF THE INVENTION

Figure 1:
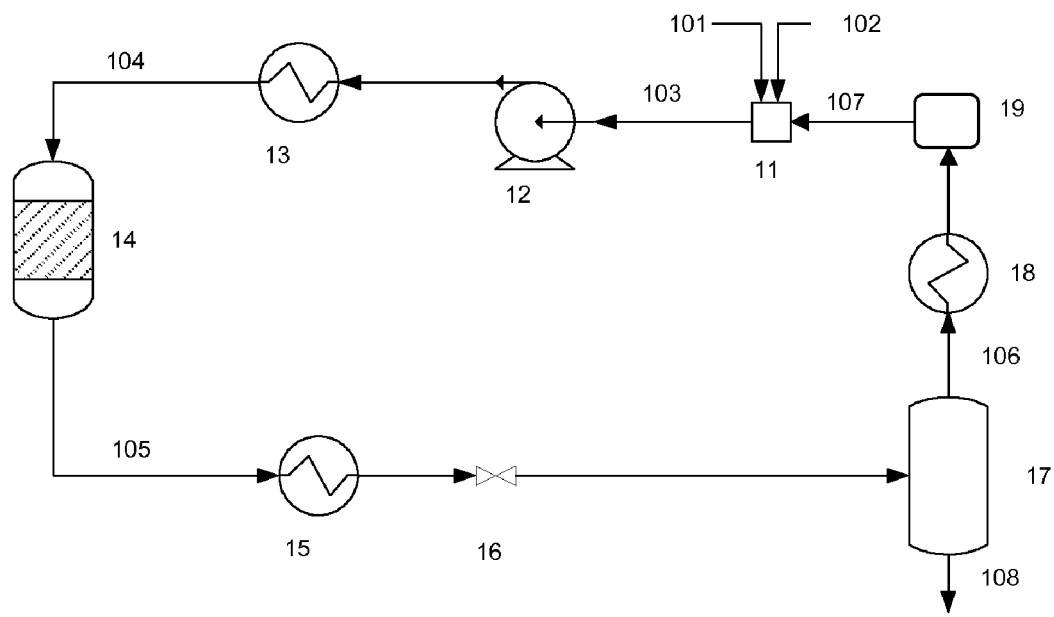
FIG. 1 and FIG. 2 represent schemes of preferred embodiments of an apparatus for transesterification of fats and oils with continuous recycling of unreacted alcohol.

Embodiments of the present invention will now be described in detail with reference to the attached figures, the invention is not limited thereto but only by the claims. The drawings described are only schematic and are non-limiting. In the drawings, the size of some of the elements may be exaggerated and not drawn on scale for illustrative purposes. The dimensions and the relative dimensions do not necessarily correspond to actual reductions to practice of the invention. Those skilled in the art can recognize numerous variations and modifications of this invention that are encompassed by its scope. Accordingly, the description of preferred embodiments should not be deemed to limit the scope of the present invention.

Furthermore, the terms first, second and the like in the description and in the claims are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Moreover, the terms top, bottom, left, right, over, under and the like in the description and the claims are used for descriptive purposes and not necessarily for describing relative positions. The terms so used are interchangeable under appropriate circumstances and the embodiments of the invention described herein can operate in other orientations than described or illustrated herein. For example, "left" and "right" of an element indicates being located at opposite sides of this element.

It is to be noticed that the term "comprising", used in the claims, should not be interpreted as being restricted to the means listed thereafter; it does not exclude other elements or steps. Thus, the scope of the expression "a device comprising means A and B" should not be limited to devices consisting only of components A and B. It means that with respect to the present invention, A and B are relevant components of the device.

For reasons of clarity, whenever in what follows the term 'oil' is used, it should be understood as having the meaning of 'oil', or 'fat', or 'fat and oil'. The oil or fat may originate from raw material or a waste stream. Even though the embodiments described below mention methanol, the same embodiments may equally well be carried out with any other alcohol, and particularly any monohydric alcohol, provided that the temperatures and pressures are adjusted according to practices known in the art.

An embodiment of the method according to the invention of producing fatty acid esters by transesterification of fats and oils is described referring to FIG. 1. A stream 101 of oils and a stream 102 of an alcohol (methanol in this particular case) are mixed in a mixing tank 11. Either one or both of the streams of oils and methanol may be preheated and/or pre-pressurized before being supplied to the mixing tank 11.

The amount of alcohol in mixture 103 should exceed the stoichiometric quantity necessary for total transesterification of the oils. In order to obtain a high yield for the reaction, the alcohol to oil ratio in mixture 103 should preferably exceed the amount of 6 mole alcohol for each mole of oil.

The resulting mixture 103 discharged from mixing tank 11 is pressurized by pump 12 and heated by heater 13 until mixture 104 at a predetermined pressure and temperature is obtained. The predetermined pressure and temperature are chosen such that the reaction mixture is heated above 240° C. and pressurized preferably between 0.5 MPa and 25 MPa.

Thereafter, the heated and pressurized oil and methanol mixture 104 is fed to reactor 14 in which the transesterification reactions occur. In order to obtain a high yield of reaction products, the mixture stream should have a predetermined residence time in the reactor 14. The transesterification reaction may be catalysed by a suitable catalyst present in reactor 14.

The reactions occurring in reactor 14 produce a reaction mixture 105, which is discharged from the reactor 14. An optional step of partial cooling of the reaction mixture in a cooler 15 may be provided. The reaction mixture 105 is then depressurized with pressure-regulator 16 and fed to a means 17 for separating the reaction mixture in two or more streams, also called a separation system or a separator. In separator 17, two streams are obtained from the reaction mixture. A first stream 106, mainly comprising unreacted methanol and a second stream 108, mainly comprising the reaction products. The first stream 106 is a vapour phase and is separated from the second stream 108, which is a liquid stream.

Due to depressurization, a reaction mixture comprising two or more phases, which are intimately mixed, can be obtained. These phases can be separated afterwards, in a separator in which the reaction mixture comes to "rest", enabling the different phases to separate, such as in a flash separator.

Said step of partial (initial or preliminary) cooling the reaction mixture is advantageously performed prior to the depressurizing step. The partial cooling step refers to a distinct cooling step and does not include the fall in temperature of the reaction mixture during the depressurizing step. During depressurization, a partial evaporation of the reaction mixture can occur, which induces an additional cooling of the reaction mixture.

By performing the partial cooling step prior to the depressurizing step, a more efficient heat exchange can be achieved, as the reaction mixture will have higher density compared to after depressurization. This also allows to reduce the size of the heat exchanger for partial cooling. Furthermore, the heat withdrawn from the reaction mixture will be available at a higher temperature, which makes that heat better suitable for heat integration.

The separation of the reaction mixture into an alcohol-rich phase and an alcohol-poor phase is preferably carried out at the pressure conditions obtained by the depressurizing step. This allows to maintain a high boiling point for the alcohol, which in turn allows to condense the alcohol at more economical temperatures.

The liquid stream 108 discharged from separator 17 may consist of multiple liquid phases and comprises reaction products. The reaction products may be purified according to state-of-the-art methods, or may be purified at high temperature for maximal energy saving.

The vapour phase 106 is condensed in a condenser 18 and buffered in a buffer tank 19. Thereafter, it may be pressurized and heated in order to have the adequate temperature and pressure for being fed as a recycled stream 107 to mixing tank 11, where it joins the "fresh" streams of oils 101 and methanol 102. The method described above is a continuous transesterification process with inline separation and recovery of methanol at a high temperature.

Figure 2:
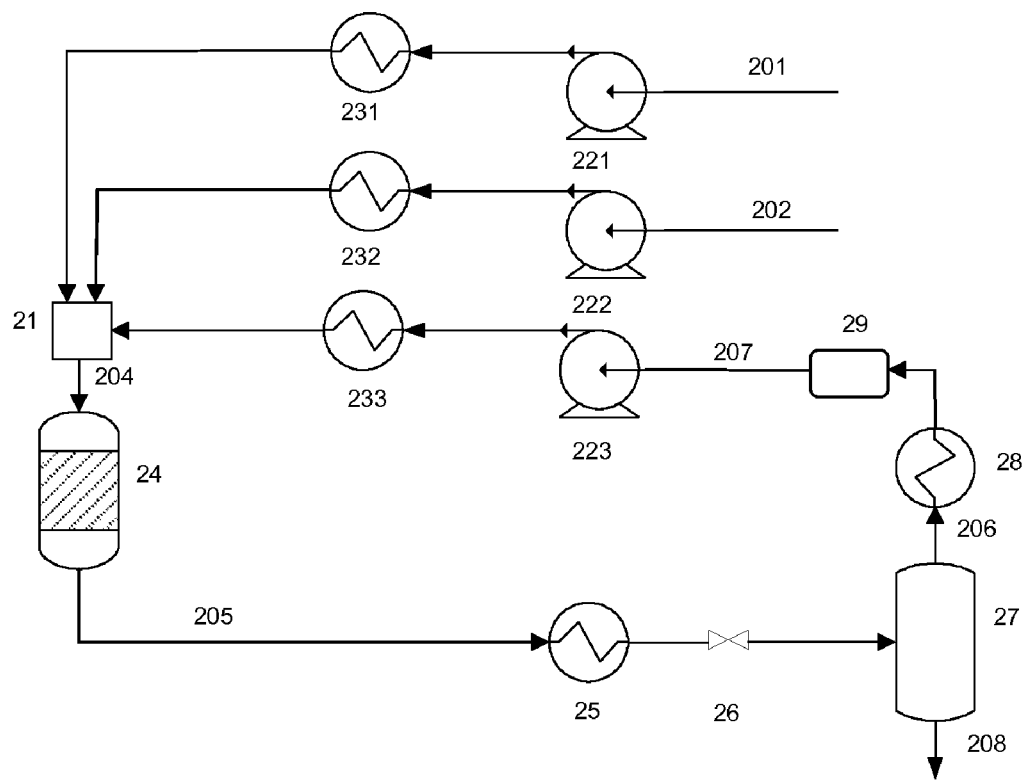

In an alternative embodiment, as depicted in FIG. 2, the various streams of oils 201, "fresh" methanol 202 and recycled methanol 207 are mixed after being heated and pressurized to the temperature and pressure needed for the transesterification reactions in reactor 24. Hence, no additional heating and pressurization occur between the mixing of the streams and the transesterification reactions.

In another alternative embodiment, the streams of "fresh" and recycled methanol are mixed before being brought to the required process conditions for reaction, while the stream of oil is fed directly to the reactor, at the same pressure and temperature as the methanol.

Figure 4:
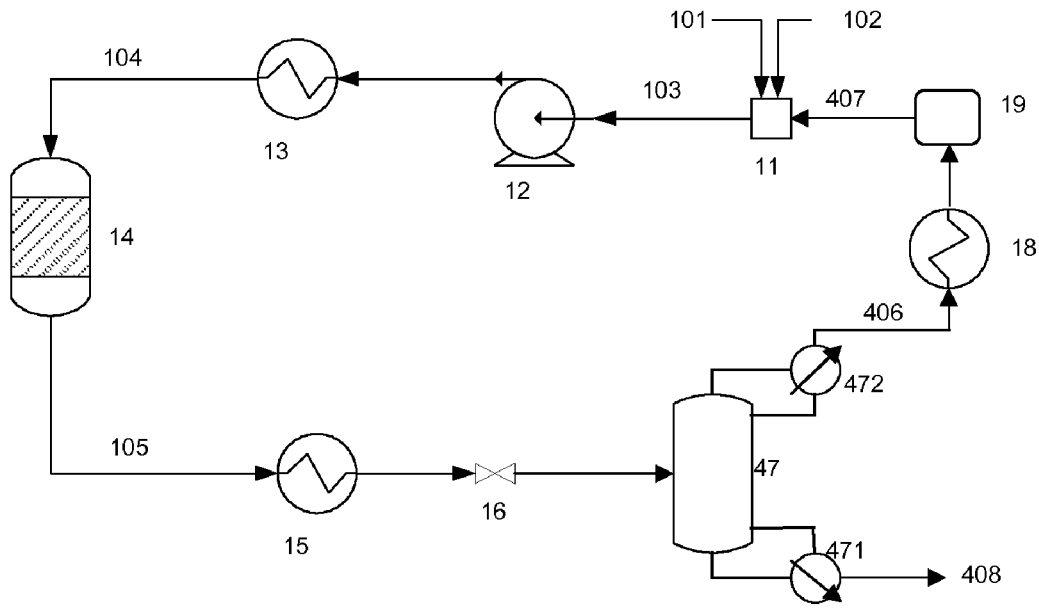
FIG. 4 and FIG. 5 represent schemes of an apparatus according to the invention using one or multiple continuous distillation systems.

In a preferred embodiment of the method according to the invention of producing fatty acid esters by transesterification of fats and oils, the separation system comprises a distillation column. Referring to FIG. 4, the reaction mixture 105, which is discharged from reactor 14, is depressurized with pressure-regulator 16 and fed to distillation column 47. An optional step of partial cooling of the reaction mixture in a cooler 15 may be provided. In the distillation column, the reaction mixture is separated into a vapour phase (top stream) 406, substantially comprising unreacted methanol and a liquid phase (bottom stream) 408, substantially comprising the reaction products.

The liquid stream 408 discharged from distillation column 47 comprises the reaction products, and may consist of multiple liquid phases. The reaction products may be purified according to state-of-the-art methods, or may be purified at high temperature for maximal energy saving.

The vapour phase 406 is condensed in a condenser 18 and buffered in a buffer tank 19. Thereafter, it may be prepressurized and preheated in order to have the adequate temperature and pressure for being fed as a recycled stream 407 to mixing tank 11, where it joins the "fresh" streams of oils 101 and methanol 102.

The method described above provides also a continuous transesterification process with inline separation and recovery of methanol at high temperature.

FIG. 1 depicts an embodiment of an apparatus for carrying out a transesterification reaction according to the invention. Such an apparatus comprises as primary components: a reactor 14 in which the transesterification reaction occurs and a separator 17 for separating a stream of unreacted alcohol from a reaction mixture discharged from the reactor 14.

The apparatus may comprise a mixing tank 11 for mixing the various streams of oil and alcohol before feeding the resulting mixture 104 to the reactor. Such a mixing tank need not be present, as the reactor 14 itself may be provided with means for mixing the various input streams of oil 101 and alcohol 102 and 107.

The apparatus of the invention comprises one or more pumps 12 for pressurizing the streams to be fed to the reactor 14 and one or more heaters or heat exchangers 13 for heating the streams to be fed to the reactor 14. Such pumps and heaters may also be provided upstream of mixing tank 11 and for each stream 101, 102 and 107 individually. The latter configuration is depicted in FIG. 2. Referring to FIG. 2, pump 222 and heater 232 bring a stream 202 of "fresh" alcohol at the required pressure, preferably between 0.5 and 25 MPa and at the required temperature, preferably above 240° C. The same occurs for stream 207 of recycled alcohol, which is brought to the required process conditions by pump 223 and heater 233. Thereafter, the three streams converge into mixing tank 21 prior to being fed to reactor 24.

Reactor 24 of FIG. 2 is identical to the reactor 14 of FIG. 1. They will be commonly referred to in the following with the numeral 14. Reactor 14 may be of any type, insofar as it has a structure to maintain the reaction mixture at the required process conditions. Preferably, reactor 14 is a tubular reactor. The feed to reactor 14 is continuous. The reactor 14 is conceived in such a way that a predetermined residence time for the oils and the alcohol in the reactor is obtained. Reactor 14 may be provided with a catalyst in order to accelerate the transesterification reaction. The catalyst in the reactor may be provided on a fixed bed or a suspension bed.

Reactor 14 discharges a reaction mixture 105 (reaction mixture 205 in FIG. 2), comprising reaction products of the transesterification reaction (e.g. glycerol, fatty acid esters) and unreacted alcohol. The unreacted alcohol needs to be separated from the reaction mixture 105. This is performed in a separation system 17 (separation system 27 in FIG. 2 and 47 in FIG. 4), in which the unreacted alcohol concentrates in the vapour phase, and the reaction products concentrate in the liquid stream, which may consist of several phases. In order to obtain an optimal separation, the apparatus of the invention may comprise a cooler or heat exchanger 15 (cooler 25 in FIG. 2) for cooling the reaction mixture 105 and/or a pressure-regulating valve 16 (valve 26 in FIG. 2) for depressurizing the reaction mixture 105.

Figure 3:
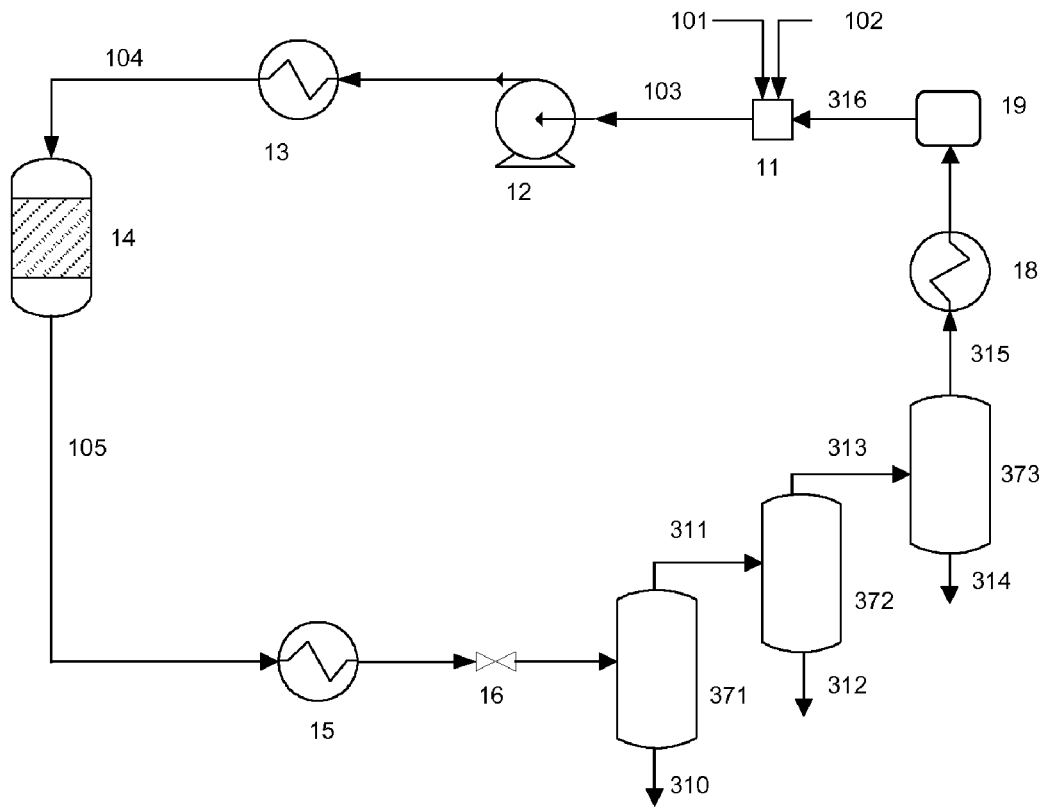
FIG. 3 represents a scheme of an apparatus according to the invention with multiple separators arranged in series.

In an embodiment of the apparatus of the invention, the separation system comprises one flash separator (separator 17 in FIG. 1, separator 27 in FIG. 2) or multiple flash separators arranged in series (separators 371, 372 and 373 in FIG. 3). In a flash separator, the feed temperature or pressure are adjusted to vaporise the feed to the desired extent. The resulting feed is collected in a vessel or drum that provides disengaging space to allow the vapour to separate from the liquid. A more detailed description of a flash separator may be found in handbooks of chemical engineering, such as Perry's Chemical Engineers' Handbook, edited by R. H. Perry and D. W. Green, published by McGraw-Hill. In the apparatus of the invention, the temperature and/or the pressure are chosen such that the alcohol is vaporised, whereas other substances (e.g. initial, intermediate or end products: oil, glycerol, methyl esters, monoglycerides, diglycerides) are substantially kept in a liquid state. In the flash separator of the invention, the vapour phase and the liquid stream are withdrawn separately and continuously.

Figure 5:
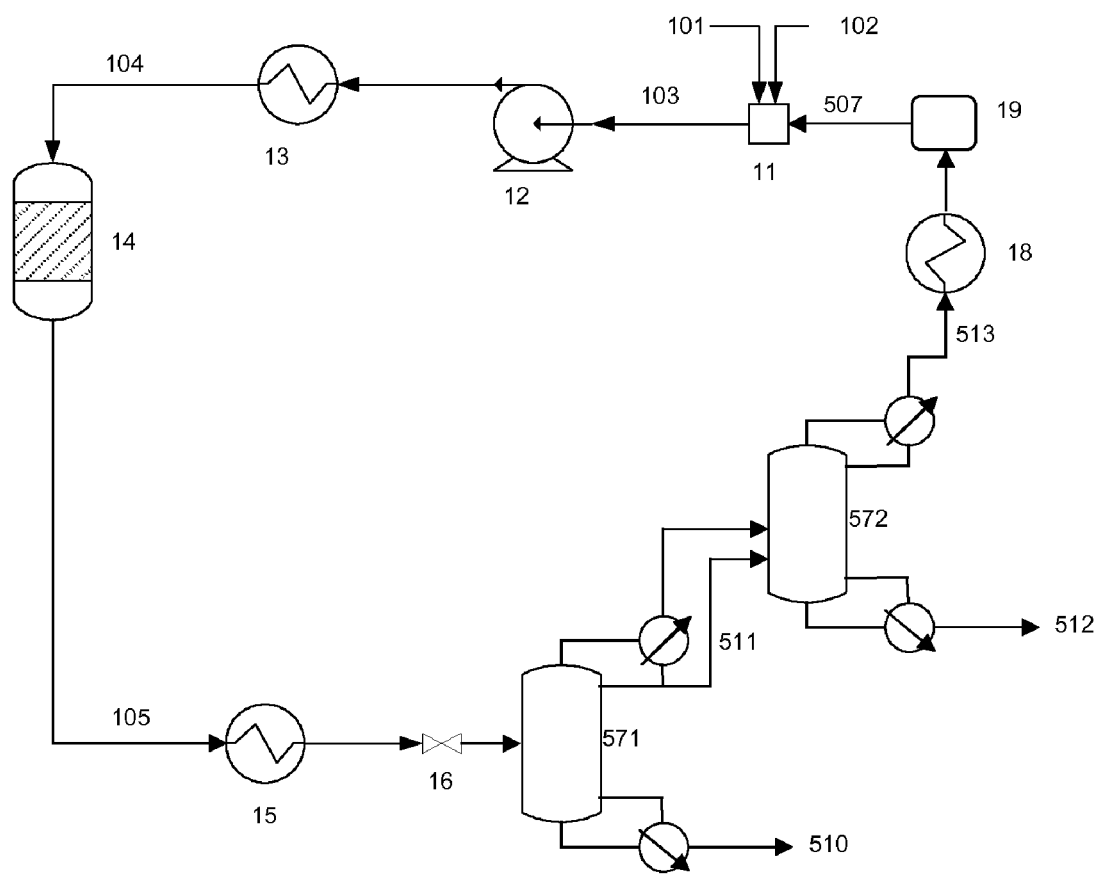

In an alternative embodiment, the separation system comprises one (multi-stage) distillation column (column 47 in FIG. 4) or several (multi-stage) distillation columns arranged in series (columns 571, 572 in FIG. 5). The distillation columns may comprise random or structured packings or trays to bring the vapour phase and the one or more liquid phases in intimate contact. Other separation systems may also be used.

The vapour phase 106 discharged from separator 17 (phase 206 discharged from separator 27) may comprise traces of other products, such as glycerol, water, fatty acid esters and mono-, di- and triglycerides. The apparatus of the invention further comprises a condenser 18 (condenser 28 in FIG. 2) in which the vapour phase 106 discharged from separator 17 is condensed into a stream 107 substantially comprising unreacted alcohol (stream 207 in FIG. 2, stream 407 in FIG. 4). The condensed stream 107 of unreacted alcohol is recycled into the process. The apparatus of the invention may comprise a buffer tank 19 (tank 29 in FIG. 2) for storing the condensed stream 107 of recycled alcohol prior to being recycled into the process.

FIG. 3 shows a scheme of an apparatus according to the invention with multiple flash separators arranged in a series. This allows to obtain a recycled stream 316 with a higher concentration of unreacted alcohol. Hence, in a first flash separator 371, the reaction mixture 105 is separated in a first vapour phase 311 and a first liquid stream 310. The first vapour phase 311 is fed to a second flash separator 372. In the second separator, the process conditions are such that part of the feed 311 is condensed and discharged as a second liquid stream 312. The remaining vapour phase 313 is fed to a third flash separator 373. Part of the feed 313 in the third separator condenses to form a third liquid stream 314. The remaining vapour phase 315 is extracted from the third separator 373 and fed to a condenser 18 and a buffer tank 19 subsequently.

Similarly, FIG. 5 shows a scheme of an apparatus according to the invention with multiple distillation columns arranged in a series. In a first distillation column 571, the reaction mixture 105 is separated in a first vapour phase (first top stream) 511 and a first liquid stream (first bottom stream) 510. The first vapour phase 511 is fed to a second distillation column 572. In the second distillation column 572, part of the feed 511 is condensed and discharged as a second liquid stream 512 (second bottom stream). The remainder 513 of the feed is collected as a second top stream (second vapour phase) 513. The second top stream 513 is fed to a condenser 18 and subsequently to a buffer tank 19. The second top stream forms the recycled stream 507 which is recycled to the reactor and substantially comprises methanol (alcohol).

All distillation columns 47, 571 and 572 may comprise a reboiler 471 and a condenser 472 to drive the distillation separation.

It is important for the method of the present invention to choose suitable values for pressure and temperature in the separation system in order to recover an optimally large amount of the unreacted methanol from the reaction mixture. The temperature and pressure in the separator should be chosen so as to shift as much methanol as possible to the vapour phase. Preferably, the ratio of methanol in the vapour phase to the total amount of methanol in the separator is equal to or larger than 0.9. However, the conditions in the separator must also be such that the fraction of other reaction mixture products in the vapour phase is as small as possible. Besides methanol, the vapour phase may also comprise fractions of glycerol, fatty acid esters, monoglycerides, diglycerides, triglycerides, etc. Of these residual fractions of other products present in the vapour phase, glycerol and—if present—glycerol degradation products are the most volatile. Preferably, the ratio of glycerol in the vapour phase to the total amount of glycerol present in the separator is equal to or less than 0.1.

The temperature in the separation system comprising only one separator or distillation column is preferably in the range between 60° C. and 350° C. (see FIGS. 1 and 2). The separation system may comprise more than one separator (flash separator or distillation column), as shown in FIG. 3. In the latter case, the temperature in the first (i.e. the most upstream) flash separator or distillation column is preferably in the range between 60° C. and 350° C., while the temperature in the subsequent (downstream) flash separator(s) or distillation column(s) lies preferably in the range between 40° C. and 100° C. The pressure in the separation system is preferably higher than 0.1 MPa, more preferably in the range between 0.2 MPa and 3 MPa. Preferred values for temperature and pressure in the separation system depend primarily on the type and the excess of alcohol used, on the presence of contaminants such as water and on the process parameters in the reactor.

In the method of the invention, the pressure and temperature of the transesterification reaction need to be chosen such that the alcohol is at a temperature above 240° C. The pressure in the reactor is preferably between 0.5 MPa and 25 MPa. The temperature in the reaction is preferably between 240° C. and 450° C. The transesterification reaction may proceed with or without a catalyst. Suitable catalysts are magnesium oxide, manganese oxide, molybdenum oxide, calcium oxide, calcium carbonate, sodium carbonate, etc. Catalysts comprising magnesium oxide are preferred.

EXAMPLE 1

With Catalyst—Supercritical Methanol

A first example refers to the apparatus and method according to FIG. 1. "Fresh" methanol is pressurized to 1.2 MPa (not shown in the figure). A stream 102 of this "fresh" methanol is fed to mixing tank 11 at a rate of 1.2 g/min. Oil is pressurized to 1.2 MPa. A stream 101 of this oil is fed to mixing tank 11 at a rate of 8.1 g/min. A stream 107 of recycled methanol at a pressure of 1.2 MPa is fed to mixing tank 11 at a rate of 3.8 g/min. The mixture 103 is pressurized to 15 MPa and heated to 300° C. Thereafter it is fed to a tubular reactor 14. The residence time in the reactor, as calculated from the density under atmospheric conditions, is 15 minutes. The reactor is provided with MgO catalyst. After this step, more than 95% of the oil is converted to bio diesel. The reaction mixture 105 discharged from the reactor is cooled to 280° C. and depressurized to 1.2 MPa. Thereafter, the reaction mixture is fed to the flash separator 17. Separator 17 is kept at a temperature of 230° C. Under those conditions, more than 92% of the unreacted methanol present in the reaction mixture is in the vapour phase. Less than 8% of the unreacted methanol present in the reaction mixture dissolves in the liquid phases. The vapour phase in separator 17 is recovered, condensed and fed to a buffer tank 19, from where it is recycled to the process. In steady-state, the recycled stream contains 92% of the total methanol present in the reaction mixture stream. It contains less than 8% of the total glycerol present in the reaction mixture stream and less than 5% of the total of the remaining products (bio diesel, mono-, di- and triglycerides). The liquid stream in separator 17 is discharged as a stream 108 at a rate of 9.3 g/min and comprises essentially bio fuel (i.e. fatty acid esters) and glycerol, with a small residual fraction of mono-, di- and triglycerides and methanol. Stream 108 is purified from its residual fractions.

EXAMPLE 2

With Catalyst—Subcritical Methanol

The second example refers to the apparatus and method according to FIG. 1. "Fresh" methanol is pressurized to 0.6 MPa (not shown in the figure). A stream 102 of this "fresh" methanol is fed to mixing tank 11 at a rate of 1.1 g/min. Oil is pressurized to 0.6 MPa. A stream 101 of this oil is fed to mixing tank 11 at a rate of 8.1 g/min. A stream 107 of recycled methanol at 0.6 MPa is fed to mixing tank 11 at a rate of 3.9 g/min. The mixture 103 is pressurized to 6 MPa and heated to 300° C. Thereafter it is fed to a tubular reactor 14. The residence time in the reactor, as calculated from the density under atmospheric conditions, is 15 minutes. The reactor is provided with MgO catalyst. After this step, the conversion efficiency from oil to bio diesel is more than 91%. The reaction mixture 105 discharged from the reactor is depressurized to 0.6 MPa. Thereafter, the reaction mixture is fed to the flash separator 17. Separator 17 is kept at a temperature of 200° C. Under those conditions, more than 94% of the unreacted methanol present in the reaction mixture is in the vapour phase. Less than 6% of the unreacted methanol present in the reaction mixture dissolves in the liquid phases. The vapour phase in separator 17 is recovered, condensed and fed to a buffer tank 19, from where it is recycled to the process. In steady-state, the recycled stream contains 94% of the total methanol present in the reaction mixture stream. It contains less than 6% of the total glycerol present in the reaction mixture stream and less than 4% of the total of the remaining products (bio diesel, mono-, di- and triglycerides). The liquid stream in separator 17 is discharged as a stream 108 at a rate of 9.2 g/min and comprises essentially bio fuel and glycerol, with a small residual fraction of mono-, di- and triglycerides and methanol. Stream 108 is purified from its residual fractions.

EXAMPLE 3

Without Catalyst—Supercritical Methanol

A third example also refers to the apparatus and method according to FIG. 1. "Fresh" methanol is pressurized to 0.5 MPa (not shown in the figure). A stream 102 of this "fresh" methanol is fed to mixing tank 11 at a rate of 0.84 g/min. Oil is pressurized to 0.5 MPa. A stream 101 of this oil is fed to mixing tank 11 at a rate of 5 g/min. A stream 107 of recycled methanol is fed to mixing tank 11 at a rate of 6.66 g/min. The mixture 103 is pressurized to 19 MPa and heated to 350° C. Thereafter it is fed to a tubular reactor 14. The residence time in the reactor, calculated to the density under atmospheric conditions, is 15 minutes. The reactor is not provided with a catalyst. After this step, more than 85% of the oil is converted to bio diesel. The reaction mixture 105 discharged from the reactor is cooled to 280° C. and depressurized to 0.5 MPa. Thereafter, the reaction mixture is fed to the flash separator 17. Separator 17 is kept at a temperature of 155° C. Under those conditions, more than 95% of the unreacted methanol present in the reaction mixture is in the vapour phase. Less than 5% of the unreacted methanol present in the reaction mixture dissolves in the liquid phases. The vapour phase in separator 17 is recovered, condensed and fed to a buffer tank 19, from where it is recycled to the process. In steady-state, the recycled stream contains 95% of the total methanol present in the reaction mixture stream. It contains less than 5% of the total glycerol present in the reaction mixture stream and less than 2% of the total of the remaining products (bio diesel, mono-, di- and triglycerides). The recycled stream contains 97 wt % methanol and 3 wt % residual products (glycerol, bio diesel, mono-, di- and triglycerides). The liquid phases in separator 17 are discharged as a stream 108 which comprises essentially bio fuel and glycerol, with a small residual fraction of mono-, di- and triglycerides and methanol. Stream 108 is purified from its residual fractions.

EXAMPLE 4

With Catalyst—Supercritical Methanol—Water Contamination

The fourth example refers to the apparatus and method according to FIG. 5. "Fresh" methanol is pressurized to 0.5 MPa (not shown in the figure). A stream 102 of this "fresh" methanol is fed to mixing tank 11 at a rate of 0.32 g/min. Waste oil containing 10 wt % water is pressurized to 0.5 MPa. The waste oil and the water are intimately mixed. A stream 101 of this oil is fed to mixing tank 11 at a rate of 2.55 g/min. A stream 507 of recycled methanol is fed to mixing tank 11 at a rate of 1.26 g/min. The mixture 103 is pressurized to 15 MPa and heated to 300° C. Thereafter it is fed to a tubular reactor 14. The residence time in the reactor, as calculated from the density under atmospheric conditions, is 15 minutes. The reactor is provided with MgO catalyst. After this step, more than 95% of the oil is converted to bio diesel. The reaction mixture 105 discharged from the reactor is cooled to 200° C. and depressurized to 0.1 MPa. Thereafter, the reaction mixture is fed to a first distillation column 571 containing 3 rectification and 3 stripping stages (respectively including stripper or condenser and reboiler). The reboiler operates at 273° C. and the condenser operates at 65° C. The liquid stream 510 (bottom stream) contains more than 99.99% of the methyl esters and the glycerol. It contains less than 200 ppm methanol. The vapour stream 511 which consists of 97 wt % methanol and 3 wt % water is fed to a second distillation column 572. This distillation column contains 14 stages. The reboiler operates at 82° C. and the condenser operates at 55° C. The top product stream 513 contains 99% of the methanol and less than 10% of the water present in the reaction mixture stream 105. The condensed top stream is fed to a collection vessel 19 from which it is re-used in the process. The bottom stream 512 comprises substantially water.

While the foregoing description and drawings represent the preferred embodiments of the present invention, it will be obvious to those skilled in the art that various changes and modifications may be made therein without departing from the spirit and scope of the present invention.

The invention claimed is:

1. A method of producing fatty acid esters by means of transesterification of fats and/or oils and an alcohol, the method comprising the steps of:
   supplying the fats and/or oils and the alcohol to a reactor,
   reacting the fats and/or oils with the alcohol at a temperature falling in the range between 240° C. and 450° C. and a pressure falling in the range between 0.5 MPa and 25 MPa to obtain a reaction mixture comprising unreacted alcohol,
   adjusting the pressure and the temperature of the reaction mixture to foam a vapour phase and one or more phases of higher density than the vapour phase, wherein the vapour phase and one or more phases of higher density are intimately mixed, and wherein the unreacted alcohol is concentrated in the vapour phase,
   feeding the mixture of vapour phase and the one or more phases of higher density to a separator and separating the vapour phase to obtain a first stream and the one or more phases of higher density to obtain a second stream, wherein the first stream comprises at least 90% by weight of unreacted alcohol and the second stream comprises a smaller fraction of unreacted alcohol than the first stream, and
   continuously recycling said first stream to the reactor.

2. The method according to claim 1, comprising a step of depressurizing the reaction mixture to a pressure equal to or higher than 0.1 MPa to form the vapour phase, wherein separation into the first stream and the second stream mixture is performed at the pressure of the depressurizing step.

3. The method according to claim 2, wherein in the depressurizing step, the reaction mixture is depressurized to a pressure falling in the range between 0.1 MPa and 1.2 MPa.

4. The method according to claim 2, wherein, in said depressurizing step, the reaction mixture is depressurized to a pressure falling in the range between 0.2 MPa and 3 MPa.

5. The method according to claim 1, comprising cooling the reaction mixture to a temperature falling in the range between 120° C. and 300° C. to form the vapour phase.

6. The method according to claim 2, wherein a step of partial cooling the reaction mixture is performed prior to the depressurizing step.

7. The method according to claim 6, wherein in the partial cooling step, the reaction mixture is cooled to a temperature falling in the range between 200° C. and 280° C.

8. The method according to claim 1, wherein in the reacting step, the fats and/or oils are reacted with the alcohol in the presence of MgO catalyst.

9. The method according to claim 1, wherein the separating step comprises separating the reaction mixture by flash separation.

10. The method according to claim 1, wherein the separating step comprises separating the reaction mixture by distillation.

11. The method according to claim 1, wherein the separating step comprises the steps of:
- separating the reaction mixture to obtain a third stream and the second stream, the third stream comprising a larger fraction of unreacted alcohol; and
- separating the third stream to obtain the first stream and a fourth stream, the first stream comprising a fraction of unreacted alcohol which is larger than the fraction of unreacted alcohol of the third stream.

12. The method according to claim 1, wherein the reaction mixture comprises water.

13. The method of claim 1, wherein at least 90% by weight of the unreacted alcohol present in the separator is in the vapour phase, and wherein the ratio of glycerol in the vapour phase to the total amount of glycerol present in the separator is equal to or less than 0.1 by weight.

14. The method according to claim 1, comprising cooling the reaction mixture to a temperature falling in the range between 60° C. and 350° C. to form the vapour phase.

15. The method according to claim 6, wherein in the partial cooling step, the reaction mixture is cooled to a temperature falling in the range between 100° C. and 300° C.

16. The method according to claim 15, wherein in the partial cooling step, the reaction mixture is cooled to a temperature falling in the range between 120° C. and 300° C.

* * * * *